United States Patent [19]
Sprouse et al.

[11] Patent Number: 5,961,985
[45] Date of Patent: Oct. 5, 1999

[54] VACCINE AND SERUM FOR ENDOTOXIN ASSOCIATED DISEASE IMMUNIZATION AND TREATMENT, DETOXIFIED ENDOTOXIN, AND BACTERIAL MUTANT

[75] Inventors: Ronald F. Sprouse; Harold E. Garner, both of Columbia, Mo.

[73] Assignee: The Curators of the University of Missouri, Columbia, Mo.

[21] Appl. No.: 08/856,432

[22] Filed: May 14, 1997

Related U.S. Application Data

[62] Division of application No. 08/126,688, Sep. 27, 1993, Pat. No. 5,641,492, which is a continuation of application No. 07/279,338, Dec. 2, 1988, abandoned, which is a continuation of application No. 06/697,008, Jan. 31, 1985, abandoned, which is a continuation-in-part of application No. 06/597,115, Apr. 5, 1984, abandoned.

[51] Int. Cl.$^6$ .................................................. A61K 39/112
[52] U.S. Cl. ................................... 424/258.1; 424/184.1; 424/147.1; 424/257.1; 424/193.1; 424/197.1; 424/278.1
[58] Field of Search ............................ 424/258.1, 184.1, 424/147.1, 257.1, 197.1, 193.1, 278.1

[56] References Cited

U.S. PATENT DOCUMENTS

| | | | |
|---|---|---|---|
| 3,075,883 | 1/1963 | Scherr et al. | 424/92 |
| 4,029,762 | 6/1977 | Galanos et al. | 424/87 |
| 4,148,877 | 4/1979 | Choay et al. | 424/92 |
| 4,242,270 | 12/1980 | Ayme et al. | 260/412.8 |
| 4,327,082 | 4/1982 | Armitage | 424/92 |
| 4,328,210 | 5/1982 | Kucera | 424/92 |
| 4,335,107 | 6/1982 | Snoeyenbos et al. | 424/93 |
| 4,338,298 | 7/1982 | Myers | 424/92 |
| 4,343,792 | 8/1982 | Gouet et al. | 424/92 |
| 4,350,684 | 9/1982 | Pardon et al. | 424/92 |
| 4,404,186 | 9/1983 | Ron | 424/92 |
| 4,491,660 | 1/1985 | Gendrich et al. | 536/32 |
| 4,495,096 | 1/1985 | Wissler | 260/112 B |
| 4,530,831 | 7/1985 | Lutticken et al. | 424/84 |
| 4,530,832 | 7/1985 | Goodnow et al. | 424/92 |
| 4,567,041 | 1/1986 | Likhite | 424/87 |
| 4,569,840 | 2/1986 | Kit | 424/84 |
| 4,571,336 | 2/1986 | Houck et al. | 424/95 |
| 4,582,790 | 4/1986 | Auerbach | 425/7 |
| 4,582,798 | 4/1986 | Brown et al. | 435/68 |
| 4,762,712 | 8/1988 | Stolle et al. | 424/92 |
| 4,789,544 | 12/1988 | Nelson et al. | 424/90 |
| 5,179,018 | 1/1993 | Bogard, Jr. et al. | 424/90 |

FOREIGN PATENT DOCUMENTS

| | | |
|---|---|---|
| 8234579 | 8/1982 | European Pat. Off. . |
| 123028 | 8/1958 | New Zealand . |
| 145121 | 5/1966 | New Zealand . |
| 149970 | 9/1967 | New Zealand . |
| 151595 | 2/1968 | New Zealand . |
| 155280 | 2/1969 | New Zealand . |
| 194448 | 7/1980 | New Zealand . |
| 164622 | 8/1971 | United Kingdom . |

OTHER PUBLICATIONS

Acres, et al. "Antigen–Extinction Profile in Pregnant Cows . . . "; Am. J. Vet. Res. vol. 43, No. 4, pp. 569–575, Apr. 1982.

Alving et al. "Mitogenic Activities of Lipid A and Liposome–Associated Lipid A: Effects of Epitope Density", Reviews of Infectious Diseases, vol. 6, No. 4, pp. 493–496, Jul.–Aug. 1984.

Chedid et al. "Immunologie—Activities Edjuvante et Mitogene de Lipopolysaccharides Detoxifies", C.R. Acad. Sc. Paris, t. 280, 3 Mars 1975.

Crosa et al. "Molecular Relationships Among the Salmonelleae", J. of Bacteriology, vol. 115, No. 1, pp. 307–315, Jul 1973.

Davis et al. "Microbiology", 3rd Edition, pp. 436, 437, 447 and 448.

Eisenstein "Evidence for O–Antigens . . . Prepared from Salmonella", Infection and Immunity, vol. 12, No. 2, pp. 364–377, Aug. 1975.

Eisenstein "Immunity To Experimental Salmonella Infection: . . . In C3H/HeJ and CD–1 Mice[1]", The Journal of Immunology, vol. 121, No. 3, pp. 1010–1014, Sep. 1978.

Fauci "Host–Defense Mechanisms Against Infection", Current Concepts, pp. 18–27.

Gaffin "Prophylaxis and Therapy With Anti–Endotoxin . . . ", Proceedings of American Assoc. of Equine Practitioners, 1982, Atlanta, Georgia.

Girotti et al. "Effects of Immunization On Cardiopulmonary Alterations Of Gram–Negative Endotoxemia", Journal of Applied Physiology; Respiration, environment, exercise Physiology 56(3); 582–589, 1984.

Goodman et al. "Selective Interaction Between Lymphocytes and Lipid A Subunits in Lipopolysaccharide Macromolecular Aggregates", Review of Infectious Diseases, vol. 6, No. 4, pp. 511–518, Jul.–Aug. 1984.

Hodgin et al., Infection (1976) 4(2) 5–10 Abstract.

Johns et al., Biol. Abs. 64:50388, 1977.

Johns et al. "Immunization With Rough Mutants of *Salmonella Minnesota* IV Protection by Antisera to O and Rough Antigens Against Endotoxin", Journal of Infectious Disease, vol. 147, No. 1, Jan. 1983.

(List continued on next page.)

*Primary Examiner*—James C. Housel
*Assistant Examiner*—Jennifer Graser
*Attorney, Agent, or Firm*—Polster, Lieder, Woodruff & Lucchesi, L.C.

[57] ABSTRACT

A combination vaccine, with methods of preparation and treatment, for protection against Gram negative bacterial diseases. The vaccine includes a killed suspension of a bacterial mutant from the taxonomic family Enterobacteriaceae, a B-lymphocyte proliferating immune modulator, and a protein and lipid binding adjuvant. A hyperimmune serum for treating diseased animals is prepared by vaccinating a donor animal with the combination vaccine and then preparing clot serum containing antigen specific antibodies. The mutant is ATCC No. 53000 and is produced by ionizing radiation of *Salmonella enteritidis*. The immune modulator is a detoxified extract of lipopolysaccharide and is useful with many antigens to enhance primary immune response.

6 Claims, 2 Drawing Sheets

OTHER PUBLICATIONS

Johnston et al. "Resistance of Neonatal Calves Given Clostrum Diet . . . ", Am. J. Vet. Res., vol. 38, No. 9, pp. 1323–1326, Sep. 1977.

Kawakami et al. "Experimental Salmonellosis", Journal of Bacteriology, vol. 92, No. 6, pp. 1585–1589, 1966.

Kwapinski, "Preparation of Antigens", Methodology of Immunochemical And Immunological Research, pp. 74, 80–81.

Kenney et al. "Antibody Response and Protection Induced by Immunization with Smooth and Rough Strains in Experimental Salmonellosis", Journal of Bacteriology, vol., 95, pp. 406–417, Feb. 1968.

Luderitz et al., "Immunochemistry of O and R Antigens of Salmonella and Related Enterobacteriaceae", Bacteriological Reviews, vol. 30, No. 1, pp. 192–255, Mar. 1966.

McCabe et al. Prog. Clin., Biol. Res., 47,107–17, (1980) Medline Abst. No. 81141080.

McCabe, "Immunization With R Mutants of *S. Minnesota*", Journal of Immunology, vol. 108, No. 3, pp. 601–610, Mar. 1972.

Moller et al., "Section II: Immunology", Bacterial Lipopolysaccharides The Chemistry, Biology, and Clinical Significance of Endotoxins, pp. 44–48.

Makela et al., "Role of O–antigen (Lipopolysaccharide) Factors in the Virulence of Salmonella", Bacterial Lipopolysaccharides The Chemistry, Biology, and Clinnical Significance of Endotoxins, pp. 73–77.

Morris, D.C., et al., Proceedings of the Conference of Research Workers and Animal Diseases—64th Annual Meeting, Chicago, Ill. Nov. 1983, Abstract 190.

Myers, L.L., "Passive Protection of Calves Against Experimentally Induced and Naturally Occurring Enteric Colibacillosis", Am. J. Vet. Res. vol. 41, No. 12, pp. 1952–1956, 1980.

Myers, L.L., "Vaccination of Cows with an *Escherichia coli* Bacterin for the Prevention of Naturally Occurring Diarrheal Disease in Their Calves", Am. J. Vet. Res. vol. 37, No. 7, pp. 831–834, Jul. 1976.

Ribi et al., "Peptides as Requirement for Immunotherapy of the Guinea–pig Line–10 Tumor with Endotoxins", Cance Immunol. Immunother. 7, 43–58, 1979.

Biological Abstracts, vol. 79, Abstract No. 13284, 1984.

Chem. Abs., vol. 76, Abstract No. 31062v, 1972.

Chem. Abs. vol. 89, Abstract No. 195284p.

Biological Abstracts, vol. 62, Abstract No. 37306, 1976.

Biological Abstracts, 70(7):4630, Abstract No. 44015, 1980.

Smith et al., "A Preliminary Evaluation of Some Preparations of *S. Typhimurium* As Vaccines In Horses", The University of Georgia, pp. 211–215, Sep. 18, 1982.

Smith et al., "Aromatic–dependent *Salmonella Typhimurium* As Modified Live Vaccines for Calves", American Journal of Veterinary Research, vol. 45, No. 1, pp. 59–66, Jan. 1984.

Takayama et al., "Separation and Characterization of Toxic and Nontoxic Forms of Lipid A", Reviews of Infectious Diseases, vol. 6, No. 4, pp. 439–443, Jul.–Aug. 1984.

Thomson, B.V.Sc., "Equine Anti–Endotoxin Hyperimmune Serum in the Treatment of Septic Arthritis in Foals", Equine Practice–Medicine/Orthopedics 6(2): 8–10, 1984.

Tizard, "The Cellular Basis of Antibody Formation", Veterinary Immunology An Introduction, 3rd Edition, pp. 67–73, 1987.

Ward et al., "Use of a Formalin–Treated, Live *Escherichia coli* Vaccine in the Prevention of Neonatal Enteric Colibacillosis in Swine", JAVMA, vol. 168, No. 4, pp. 317–318, Feb. 1976.

White, "Concepts of the Mechanism of Action of Adjuvants", Immunogenicity, pp. 112–113, 1972.

Wilkinson et al., "Non–Smooth Mutants of *Salmonella Typhimurium:* Differentiation by Phage Sensitivity and Genetic Mapping", Journal of General Microbiology, 70, pp. 527–554, 1972.

Young et al., Cross–Protective Immunity to Gram–Negative Bacilli: Studies with Core Glycolipid of *Salmonenna Minnesota* and Antigens of *Streptococcus Pneumoniae*, Journal of Infectitious Diseases, vol. 156, pp. S174–S180, Aug. 1977.

Ziegler et al., "Treatment of Gram–Negative Bacteremia and Shock With Human Antiserum to a Mutant *Escherichia Coli*", New England Journal of Medicine, vol. 307, No. 20, pp. 1225–1230, Nov. 11, 1982.

"Methods In Immunology and Immunochemistry", pp. 28–31, 1967.

"Methods In Immunology and Immunochemistry", pp. 64–69, 1967.

McCabe, T. Inf. Dis., 136, 5161–6, (1977).

Morrison et al. Adv. Immunol., vol. 28, pp. 294–450 (1979).

Crosa et al. J of Bact 155:307–325 1973.

Galanos et al. International Review of Biochemistry, Biochemistry of Lipids II, vol. 14 only pp. 250, 251, 254, 255–259.

Sonnenwirth, in Microbiology 3rd Edition, Chapter 31, p. 647.

Collins et al. Infect & Immunity 6:451–458 1971.

Thomson, et al. "The Use of Equine Anti–Endotoxin Hyperimmune Serum . . . " Journal of the South African Veterinary Association 54:259–281, 1983.

Hodgin et al. 1976. Infection 4(1):5–10.

VACCINE AND SERUM FOR ENDOTOXIN ASSOCIATED DISEASE IMMUNIZATION AND TREATMENT, DETOXIFIED ENDOTOXIN, AND BACTERIAL MUTANT

REFERENCE TO THE PRIOR APPLICATION

This is a divisional of application Ser. No. 08/126,688, filed on Sep. 27, 1993 now U.S. Pat. No. 5,641,492, which is a continuation of U.S. patent application Ser. No. 07/279,338 filed Dec. 2, 1988 (now abandoned); which is a continuation of U.S. patent application Ser. No. 06/697,008 filed Jan. 31, 1985 (now abandoned); which is a continuation-in-part of application Ser. No. 06/597,115 filed Apr. 5, 1984, now abandoned.

BACKGROUND OF THE INVENTION

This invention relates to a vaccine and serum for immunization against, and treatment for, gram negative bacteria diseases. More specifically, this invention relates to a bacterial mutant of *Salmonella enteritidis* and its use in a combination vaccine to immunize mammals and birds against diseases caused by endotoxin producing gram negative bacteria in the taxonomic family Enterobacteriaceae. This invention also relates to a detoxified endotoxin immune modulator useful in the treatment of animals and men in combination with other antigens.

In the field of animal husbandry, endotoxin associated diseases pose serious animal health problems and consequently, represent an economic influence of significant proportion.

In horses, endotoxin-associated diseases include founder (i.e., laminitis), colic (i.e., abdominal crisis associated with dietary engorgement and other stressful phenomena such as abdominal obstruction, intestinal ischemia, Gram negative bacterial enteritis/diarrhea, intestinal malabsorption, transport stress, parturition, etc.) septic arthritis, and Gram negative intrautrine infections. Endotoxin-associated diseases in cattle include laminitis in both dairy and feedlot cattle, sudden death syndrome in feedlot cattle, mastitis in dairy cattle, and dysentery, white scours or colibacillosis, and Salmonella diarrhea in baby calves. Endotoxin-associated disease in swine include parturition dysagalactia (i.e., mammary gland failure related to Gram negative endometritis), intestinal edema disease, and baby pig Salmonella diarrhea. Salmonella diarrhea, hemorrhagic septicemia, infection of the air sacs and sinuses; and fowl cholera and other Pasteurelloses are examples of endotoxin-associated diseases of birds.

Previous treatment for endotoxin mediated and/or associated diseases has been retrospective (i.e., after development of clinical illness) and has been limited to chemotherapeutic intervention. Prevention measures were not achieved with such treatment. Prior limited, definitive, vaccinal protection from Gram negative septicemia and/or endotoxemia has been accomplished only via (a) individualized vaccines comprised of autogenous bacterial isolates expressing various antigenic epitopes (K-antigens or O-carbohydrate Bide chains) or (b) live vaccines comprised of attenuated or deletion-modified, live bacterial isolates.

The major disadvantage of the current methodologies for treating endotoxin mediated and/or associated diseases is that such treatments are initiated only after clinical illness has developed, which frequently is after the disease has attained an irreversible state. The prior vaccinal protection for Gram negative septicemia and/or endotoxemia that has been reported for individualized vaccines comprised of autogenous bacterial isolates is not time, cost or production efficient because such vaccines are produced retrospectively, after disease has developed.

The primary disadvantages of the polyvalent vaccines comprised of multiple bacterial isolates expressing various antigenic epitopes (K-antigens or O-carbohydrate side chains) are that the bacterial isolates causing disease at any given time are subject to epidemiological shifts and/or drifts in antigenic epitopes causing a change in antigenic specificity and thus loss of protective efficacy. The K-antigens or O-carbohydrate side chains also are potent stimulators of immunoglobulin IgE which is responsible for undesirable anaphylactoid reactions in many animal species, especially the horse.

The primary disadvantages of live vaccines comprised of attenuated or deletion-modified bacterial isolates is that they have the potential for reversion to the wild-type parental strains and thus resumption of pathogenicity for vaccinated animals.

Accordingly, a long felt need exist s for a vaccine and serum to immunize and treat against diseases caused by Gram negative bacteria and to overcome the deficiencies found in the prior art. One principal object of this invention is to meet this need.

SUMMARY OF THE INVENTION

An immune modulator which is non-toxic to mammals, including man, has been developed which, when used with another antigen to immunize such mammals, enhances rapid and elevated antibody responses.

A combination vaccine and hyperimmune serum was developed for protection of horses and cattle against endotoxin-associated diseases. The vaccine also has potential for protecting other animals such as swine and sheep, and birds against similar bacterial and/or endotoxin-associated diseases.

The vaccine comprises a killed suspension of a non-O-carbohydrate side chain bacterial mutant, an immune modulator with propensity for B-lymphocyte proliferation and a carrier having high lipophilic and proteinophilic affinity. For immunization, the vaccine is administered intramuscularly or subcutaneously at concentrations having at least $1\times10^7$ bacteria and 100 micrograms immune modulator. For treatment of an animal having a Gram negative bacterial caused disease, serum is prepared from a vaccinated donor and administered to provide a protective level of antibodies.

A mutant of a Salmonella organism is especially effective as the bacterial mutant and a method of making such mutant is disclosed.

A principal object of the invention is to provide a detoxified endotoxin immune modulator useful in enhancing antibody responses when inoculated into a mammalian host and a method of making and using such immune modulator.

Still a further object of the invention is to provide a bacterial mutant of a Salmonella organism useful alone and in combination with said immune modulator in the vaccination of animals against Gram negative bacterial diseases.

Another object of the invention, accordingly, is to provide a safe, effective and economical vaccine for protection against Gram negative bacterial diseases.

Still another object of the invention is to provide a method for preparing a safe, effective and economical vaccine for protection against Gram negative bacterial diseases.

Yet another object of the invention is to provide a method for immunization against Gram negative bacterial diseases.

An additional object of the invention is to provide a method for treating an animal infected with a Gram negative bacterial disease.

A further object of the invention is to provide a serum for the safe, effective and economical treatment of an animal infected with Gram negative bacteria.

Other and further objects of the invention together with the features of novelty appurtenant thereto, will appear in the course of the following description.

DETAILED DESCRIPTION OF THE INVENTION

The present invention involves several different concepts, namely, (1) a bacterial mutant, specifically a non-O-carbohydrate side chain bacterial mutant from the family Enterobacteriaceae; (2) a vaccine featuring bacterial mutant and a protein and lipid binding carrier and preferably including an immune modulator which is a detoxified endotoxin; (3) the aforesaid immune modulator and the method of preparing it, the immune modulator being useful in many applications, including man, and in combination with different active ingredients to increase the speed and amount of antibody response in the person or animal being treated; (4) a hyperimmune serum for treating Gram negative bacterial diseases and a method of using said serum.

The concept of broad spectrum protection via a combination vaccine per se, and/or combination vaccine-elicited hyperimmune serum against bacteremias and/or endotoxemias mediated and/or associated with a wide variety of Gram negative bacteria is an economical breakthrough for the animal industry using new molecular concepts in applied immunology. Diseases for which protection is developed by the combination vaccine includes those associated with endotoxin disseminated intravascular coagulation and, more particularly, the Gram negative bacteria *Salmonella enteritidis, Salmonella typhimurium, Salmonella typhosa, Salmonella minnesota, Salmonella abortus-equi*, and *Escherichia coli*.

The development of protection accrues from a combination vaccine of (a) a bacterial mutant with broad protective potential; (b) an immune modulator with specific propensity for B-lymphocytes and, consequently, the earlier occurrence of higher levels of neutralizing and opsonizing antibodies of high antigenic affinity and avidity and; (c) a carrier of high lipophilic and proteinophilic affinity, thus insuring uniform component suspension and prolonged antigenic release. The hyperimmune serum, derived from the combination vaccine, offers a new treatment mode, heretofore unavailable for clinical use.

Other aspects of our invention include the combination of the mutant and a carrier alone which is effective, but not on the whole as effective as the three component vaccine which includes the immune modulator.

The immune modulator itself is prepared by detoxifying extracted lipopolysaccharide. It is useful in the vaccine of this invention and also in admixture with other active ingredients, particularly antigens, to enhance the speed and amount of antibody responses and potentiates production of wide ranges of immunologic specificities. The immune modulator is non-toxic to man and other mammals.

MUTANT

Figure 1:
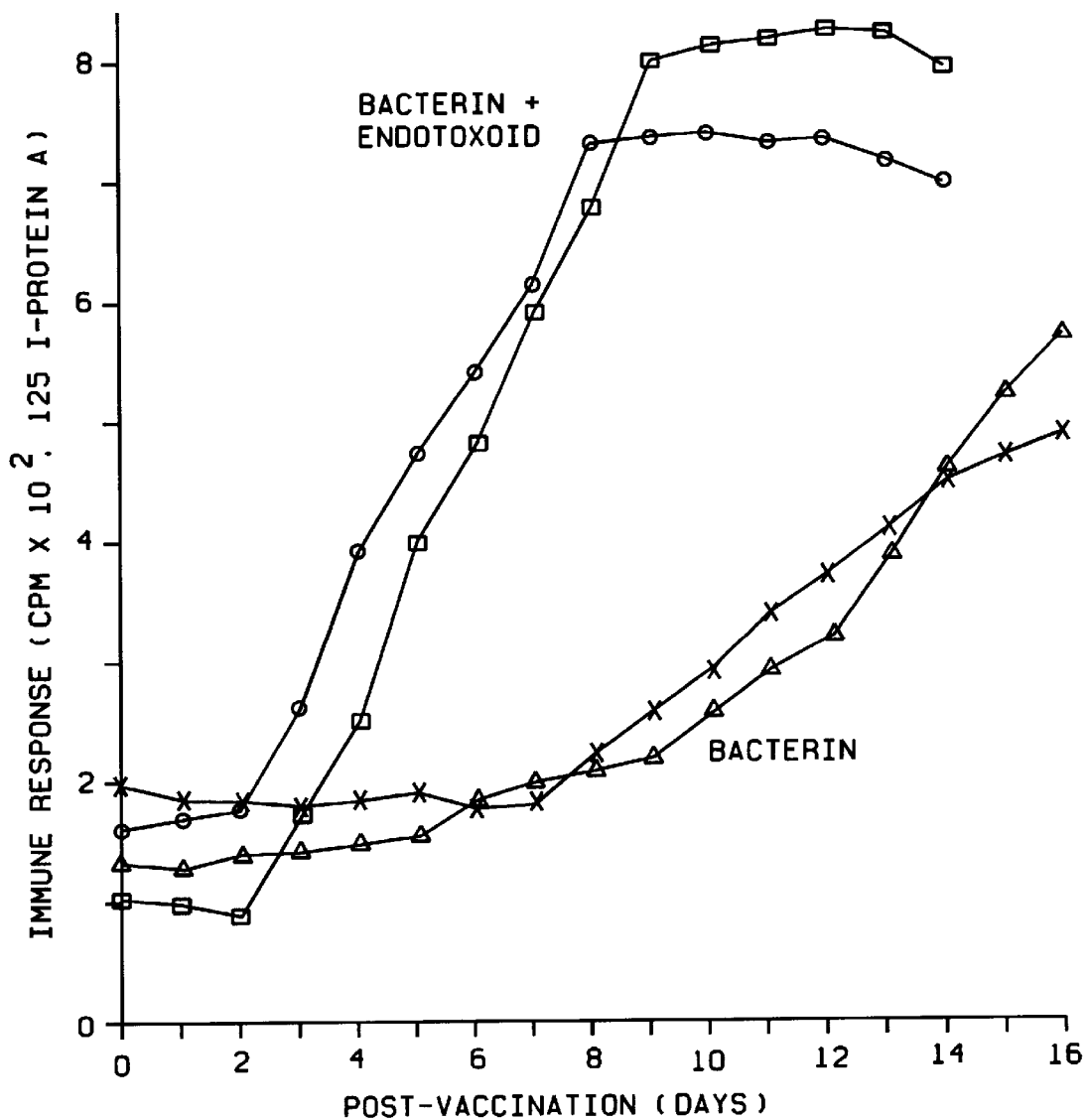
FIG. 1 is a graph depicting immune response over time of the bacterin compared to bacterin+endotoxoid preparation.

The mutant is deposited in the American Type Culture Collection as ATCC No. 53000. The date of deposit is Jan. 16, 1985, 12301 Parklawn Drive Rockville Md., 20852.

The parent isolate used to prepare the genetically modified Mutant Strain R-17 was isolated from an active diarrheal infection of a horse at the University of Missouri College of veterinary Medicine. The original clinical isolate was isolated on MacConkeys Agar, exhibiting a lactose negative, smooth, mucoid glistening colony of 3.5–4 mm diameter at 24 hours incubation at 37 C. Biochemical analysis using an API System (API Laboratory Products, 200 Express St., Plainview, N.Y. 11803) in conjunction with the API Profile Recognition System and characterization on routine laboratory media identified the original clinical isolate as *Salmonella enteritidis* (Serotype B-typhimurium). This organism is described by Ewing and Martin. (Ewing, W. H. and W. J. Martin: Enterobacteriaceae. In Manual of Clinical Microbiology, 2nd ed. Washington, American Society for Microbiology, 1974).

A specific embodiment of the organism of this invention relates to a deletion mutant strain of the parent isolate of *Salmonella enteritidis* (Serotype B-typhimurium) effected by ionizing radiation. Ionizing radiation, by virtue of high energy penetrance, induces free radical formation which labilizes cytoplasmic molecules causing single-stranded breaks in the deoxyribonucleic acid molecules, thus resulting in a high frequency of deletion mutations. Surviving mutants frequently phenotypically express various degrees of inability to synthesize intact lipopolysaccharide. Such mutants are easily recognized, since they exhibit smaller diameter, flat, rough (R) colonies, in contrast to large, punctate or convex, smooth (S) colonies produced by the parent bacterium.

X-ray mutagensis was accomplished on standard pour plates seeded with viable parent bacteria. Plates were irradiated in 5 second increments to a maximum of 35 seconds using a Machelett OEG 60 X-ray tube with beryllium window, operated at 50 kV peak and 25 mA, to give a dose rate of 250 rad/sec. Irradiated plates were held at 4 C. for 2–4 hours and then incubated in the dark at 37 C. to preclude Photoreactivation. At the end of 24 hours incubation plates were examined for a change in colonial morphology. Colonies of equal or less than 2 mm diameter exhibiting rough (R) morphology were selected, passaged at least 10 times on solid plate media, and passaged at least 3 times by intraperitoneal inoculation of laboratory mice to insure stable rough (R) phenotypic expression. Mutant strain R-17 was assayed for avirulence, in comparison with the parent isolate by a standard mouse potency assay via intragastric inoculation. Purified lipopolysaccharide from the mutant strain R-17 and the parent isolate were analyzed chemically by electrophoresis in 2% sodium dodecyl sulfate—10% polyacrylamide gels (Palva, E. T & P. Helena Makela, 1980, Lipopolysaccharide Heterogeneity in *Salmonella typhimurium*, Analyzed by Sodium Dodecyl Sulfate Polyacrylamide Gel Electrophoresis, European Journal of Biochemistry 107:137–143) and biologically by the chromatogenic limulus lysate assay (Webster, C. J. 1980, Principles of a Quantitative Assay for Bacterial Endotoxins in Blood That Uses Limulus Lysate and a Chromogenic Substrate, Journal of Clinical Microbiology 12(5):644–650), and seroagglutination (Lindberg, A. A. & L. Le Minor. 1984, Serology of Salmonella. Vol. 15, pp. 1–141; In *Methods in Microbiology*, T. Bergan, Editor, Academic Press, New York, 1984) and no O-carbohydrate antigen could be detected. Therefore, the mutant strain R-17 was presumed to be a Chemotype I or II, naked-core mutant and a novel embodiment of this invention.

Trichloroacetic Acid Extraction (Boivin Method) of Lipopolysaccharide

Lipopolysaccharide (LPS) is extracted from either acetone dried bacteria or wet bacteria suspended in 5 volumes of distilled $H_2O$ with 0.25 N aqueous Trichloroacetic Acid. The solubilized LPS (supernatant) is separated from residual bacteria (pellet) by centrifugation (5000×g, 30 min, 40° C.). The pH of the supernatant is adjusted to pH 6.8 with 10N NaOH and LPS then precipitated from the supernatant by the addition of 2 volumes of cold absolute ethyl alcohol. The precipitated LPS is collected and washed (3×) with cold absolute ethanol by centrifugation (10,000×g, 1 hr, 4° C.), lyophilized, and stored at 4° C. until use.

Preparation of the Immune Modulator

Trichloroacetic acid extracted lipopolysaccharide (LPS) is dissolved in 100 volumes of freshly prepared pyridine, 90% formic acid (2:1 v/v) by slowly increasing the temperature to the boiling point and holding for approximately 15 minutes or until apparent clearing. Detoxification then is accomplished by the addition of an equal volume of distilled $H_2O$ to the LPS-pyridine-formic acid solution and refluxing for 60 minutes. The detoxified LPS is precipitated overnight (4° C.) by the addition of 4 volumes of cold absolute ethanol and centrifugation (10,000×g, 1 hr, 4° C.), washed (3×) with cold absolute ethanol and then lyophilized detoxified LPS immune modulator was stored at 4° C. or reconstituted in 0.1% aqueous triethylamine for immediate use in effecting immune potentiation.

Potentiation of Immune Response & Hybridoma Fusion with Immune Modulator

Purified lipopolysaccharide is known to effect lymphocyte blastogensis in vitro, i.e., cultured tissue cells. In man and other mammals lymphocytes produce the interleukins (IL-1, IL-2) which mediate the immune response and thereby the production of antibodies, via the ecosatetraenoic acid metabolites (i.e. prostanoids or prostaglandins). It is also known that purified lipopolysaccharide potentiates IL-1 and prostacylin synthesis in vivo. However, purified lipopolysaccharide or in situ (associated with Gram negative bacteria per se) lipopolysaccharide possess intact O-carbohydrate side chain antigens which are toxic when introduced in vivo (i.e. into mammals), causing untoward febrile responses, coagulopathies, and sometimes fatal disseminated intravascular coagulation via anaphylactoid reactions in the sensitized host. Purified lipopolysaccharide also is cidal to mammalian tissue or cells grown in vitro culture, at picogram and low nanogram concentrations.

Embodiments of this invention include: 1) a novel method for preparation of an immune modulator which is non-toxic to mammals and tissue cell cultures, 2) a novel method employing the immune modulator for immunizing mammals to either particulate or soluble antigens which enhances more rapid and greatly elevated antibody responses and also potentiates recognition of broader spectra of antigenic determinants (epitopes) and consequent production of wider ranges of immunologic specificities, and 3) a novel method for enhancing the frequency of hybridization between antibody synthesizing-plasmacytoma cells and B-lymphocytes in cell culture from 15–30% to greater than 85% by primary immunization of donor mammals with particulate or soluble antigens in the presence of immune modulator.

Immune modulator, when given simultaneously with antigen, enhances the primary immune response of C57BL/6J mice. Enhancement occurs both with particulate antigens such as *Pseudomonas aeruginosa* and with soluble antigens such as keyhold limpet hemocyanin. Animals injected with antigen and immune modulator simultaneously demonstrated higher antibody titers at 7, 14, and 35 days after injection than did animals receiving antigen alone. Immune modulator not only enhances antibody titers early in the immune response, but more importantly, appears to prolong high serum antibody levels. Enhancement of the specific antibody response by immune modulator is not significantly affected by route of injection, since enhancement is observed when antigen and immune modulator are injected intravenously, intraperitoneally, or subcutaneouly in incomplete Freund's Adjuvant.

These results are summarized in Table A. In these experiments 5 female animals were in each group. Experimental animals received antigen and immune modulator (75 μg/dose) and controls received an equal amount of antigen and sterile saline. Serum antibody titers were measured by an indirect ELISA assay.

Immune modulator demonstrates no toxicity as assayed by its effect on cell culture growth. When SP2/0 mouse myeloma cells were cultured with immune modulator at concentrations of 100, 10, 1, 0.1 ng per ml of culture fluid, cultures with immune modulator reached cell densities equivalent to or slightly greater than the corresponding control cultures. Myeloma cells were cultured in RPMI 1640 media supplemented with 10% fetal bovine serum 2%, L-glutamine, 1% sodium pyruvate, and antibiotics. Immune modulator was added at appropriate concentrations to the media as a sterile, aqueous solution. Cell densities were determined at 24, 48, 72, and 96 hours after the addition of immune modulator or an equivalent volume of sterile distilled water.

TABLE A

Immunization of C57BL/6J Mice with Particulate or Soluble Antigens with and without Immune Modulator by Various Routes of Inoculation

| Animal Group | Antigen | Route of Inoculation | Antibody Titers After Immunization | | |
|---|---|---|---|---|---|
| | | | 7 days | 14 days | 35 days |
| Immune Modulator | P. aeruginosa | Intravenous | *1:32,000 | 1:128,000 | 1:32,000 |
| Control | P. aeruginosa | Intravenous | 1:8,000 | 1:16,000 | 1:4000 |
| Immune Modulator | P. aeruginosa in incomplete Freund's | Subcutaneous | 1:4,000 | 1:16,000 | 1:16,000 |
| Control | P. aeruginosa in incomplete Freund's | Subcutaneous | 1:2,000 | 1:4,000 | 1:2,000 |

TABLE A-continued

Immunization of C57BL/6J Mice with Particulate or Soluble Antigens with and without Immune Modulator by Various Routes of Inoculation

| Animal Group | Antigen | Route of Inoculation | Antibody Titers After Immunization | | |
|---|---|---|---|---|---|
| | | | 7 days | 14 days | 35 days |
| Immune Modulator | hemocyanin | Intraperitoneal | 1:16,000 | 1:256,000 | 1:64,000 |
| Control | hemocyanin | Intraperitoneal | 1:4,000 | 1:64,000 | 1:16,000 |

*Dilution of Sera

The Vaccine

The vaccine comprises a bacterial mutant (bacterin), an immune modulator (endotoxoid) and a protein and lipid binding carrier (adjuvant). The vaccine is administered intramuscularly or subcutaneously at concentrations equal to or greater than $1 \times 10^7$ bacteria (preferably, $1 \times 10^{10}$ bacteria), 100 or greater micrograms (preferably 100 to 4000 micrograms) detoxified endotoxin, in a lipophilic-proteinophilic absorbent carrier.

The bacterin preferably consists of a killed suspension of a non-O-carbohydrate-side chain mutant of *Salmonella enteritidis*. The bacteria may be prepared by inoculation of sterile, enriched broth with a subculture of the *Salmonella enteritidis* mutant and aerobic incubation at 37° C. to obtain maximal bacterial mass. The bacteria are killed by addition of a bactericidal agent such as merthiolate. The bacteria are checked for non-viability, then washed (4×) with sterile, non-pyrogenic physiologic saline, and reconstituted to the desired stock concentration for admixing with the other components of the vaccine.

The detoxified endotoxin is prepared by admixing Gram negative bacterial endotoxin to pyridine-formic acid (2:1) solution. The endotoxin-pyridine-formic acid mixture is thoroughly mixed in a sterile reflux condenser apparatus, the temperature increased to the boiling point and refluxed to obtain optimal methylation of endotoxin. The methylated, detoxified endotoxin then is precipitated from the aqueous reflux mixture by the addition of alcohol, collected by centrifugation, washed by resuspension in alcohol and recentriguation, and, finally, dissolved in nonpyrogenic distilled water to the desired stock concentration for admixing with the other components of the vaccine.

The adjuvant consists of high affinity lipophilic and proteinophilic carrier sufficient to absorb the protein-moiety of the bacterin and lipid-moiety of the detoxified endotoxin. Preferably the adjuvant is a fatty acid based adjuvant, oil based adjuvant, or alum based adjuvant (such as dialuminum trioxide). The carrier properties of dialuminum trioxide function by maintaining uniform suspension and allow prolonged release of the bacterin and detoxified endotoxin, thus insuring maximal antibody production. When dialuminum trixoide is utilized as the high affinity proteinophilic and lipophilic adjuvant, approximately 1.5% by volume is optimal.

Normal horses when immunized with the combination vaccine developed antibodies in their blood stream sufficient for protection when challenged in the laboratory by overfeeding with carbohydrate (i.e. dietary engorgement mimicking what occurs in nature) or intravenous injection of bacterial endotoxins (i.e., artificially induced disease mimicking what occurs in nature). Normal cattle when immunized with the vaccine developed antibodies; and exhibited no rise in body temperature, or abnormal increase in numbers or types of white cells. The advantages of the combination vaccine include (a) the mutant bacterium which is devoid of components normally present in its cell wall which cause undesirable anaphylactoid reactions; (b) an adjuvant or carrier which insures prolonged release of bacterin and/or detoxified endotoxin and consequently maximal production of neutralizing antibodies, and (c) the detoxified endotoxin which itself enhances the production of an earlier and higher level of the desirable neutralizing antibodies against intact endotoxin and bacteria. The combination vaccine, also has the quality of providing broad spectrum protection against many Gram negative bacterial diseases, since the basic structure of the antigen in common to most Gram negative bacteria; yet is devoid of those components present in existing vaccines which cause undesirable anaphylaxis.

Laboratory observations indicate that carbohydrate overload causes increased concentrations of acid in the gut (i.e., large bowel), which in turn damages the normally impermeable bowel lining and simultaneously decreases the number of Gram negative bacterial normally present in the contents and lining of the bowel by enhancement of migration into the blood stream (septicemia) and acid killing in the gut per se. The killing of these bacteria, results in the release of endotoxin from their cell walls, which in turn, also cross the acid-damaged gut lining into the blood stream. The endotoxin in the blood stream then causes undesirable blood clots in the small blood vessels (intravascular coagulation). In the case of horses and other hoofed animals, these undesirable blood clots form in the small blood vessels, ultimately causing death of the hoof tissue, permanent crippling and/or death of the animal.

The specific advantages of the combination vaccine; horses is to prevent the crippling and killing effects of founder or colic, by neutralizing endotoxin and/or Gram negative bacteria that gets into the blood stream of horses experiencing accidental overfeeding, grass founder, or stress. The specific advantage of the combination vaccine in cattle also is to prevent or reduce the endotoxin associated diseases by neutralizing any endotoxin and/or Gram negative bacteria that gain entrance to the blood stream or other tissues. Sudden death syndrome in feedlot cattle, mediated by endotoxin from Gram negative bacteria of gut origin, is a classic example of such a disease with current, immense economic implications in the cattle industry.

Potency and Safety of Vaccine Components

Extensive testing has been conducted to establish the potency and safety for the components of the vaccine.

It was discovered that incorporation of the immunoregulator endotoxoid with bacterin would elicit an earlier, and enhanced immune responsiveness in vaccinated animals. Groups of healthy adult horses and ponies were vaccinated intramuscularly with bacterin+endotoxoid or the bacterin alone. Blood samples had been drawn on the animals a week before the start of the experiment and immune profiles indicated all were normal (i.e., no history of chronic laminitis). Serum samples were collected at 24 hours intervals after immunization, and antibody titers ascertained using the antigen-specific, solid-phase radioimmunoassay. The data presented in FIG. 1 indicates that animals vaccinated with the bacterin+endotoxoid developed detectable antibody titers as soon as 3 days after vaccination compared to 7 days for those animals receiving the bacterin alone. Examination of the immune response curves in FIG. 1 between days 3 and 14 indicated a steeper slope for the bacterin+endotoxoid groups compared to the bacterin-only groups. This indicated an enhanced rate of antibody production for the former. Consequently, it was postulated that the bacterin+endotoxoid groups developed earlier protection. Additionally, an overall greater degree of protection resulted due to higher concentrations of neutralizing and/or opsonizing antibodies in their circulation, compared to those animals receiving the bacteria alone.

Endotoxoid (i.e., detoxified endotoxin) was administered to mice, horses and ponies, and cattle to ascertain the maximal amount of endotoxoid that could safely be incorporated with the bacterin, as an immunoregulator in the vaccine. An $LD_{50}$ for CF-1 mice usually is attained within 72–96 hours by intravenous injection of 0.3–0.6 mg of native endotoxin.

Groups of male, CF-1 mice (15–20 grams) were inoculated in the marginal tail vein with 0.1 milliliter physiologic saline, 300 μg of endotoxin in 0.1 of physiologic saline, and respective concentrations of 600 μg, 6000 μg, and 12,000 μg of endotoxoid in 0.1 milliliter of physiologic saline. The mice were observed at 24 hour intervals for adverse effects and mortality. Deaths were observed in the endotoxin (positive control) group by 48 hours with maximal mortality (56%) recorded at 72 hours (Table 1). In comparison no mortality was observed for the group receiving twice (600 ug) that amount of endotoxoid; only 17% mortality occurred in the group receiving the 20× (6000 μg) endotoxoid; while 40× (12,000 μg) of endotoxoid resulted in an $LD_{53}$. It was concluded that the endotoxoid was at least forty times less toxic than its native endotoxin.

TABLE 1

Comparison of Endotoxoid and Endotoxin in CF-1 Mice

| Groups of CF-1 Mice receiving: | Concentrations of μg in 0.1 ml, IV | Survival |
|---|---|---|
| Endotoxin | 300 | 44 |
| Placebo | Physiologic Saline | 100 |
| Endotoxoid | | |
| Conc. 1 | 600 | 100 |
| Conc. 2 | 6,000 | 83 |
| Conc. 3 | 12,000 | 47 |

Adult horses and ponies were inoculated intramuscularly with up to 5 mg of endotoxoid. The animals were observed twice daily for 4 days for pyrogenicity, loss of peripheral perfusion elevated heart rate, blood pressure, lethargy, and diarrhea. None of the animals receiving the 2.5 mg dose exhibited any adverse symptomology. A few of the animals inoculated with the mg dose experienced transient rise in temperature to 103–105° F. slight elevation in heart rate and mild loss of peripheral perfusion. These symptoms subsided within 8–12 hours. None of the animals developed diarrhea, blood dyscrasias or other irreversible effects. It was concluded that up to 2.5 mg (2500 μg), or 25 times the 100 μg of endotoxoid proposed for incorporation as an immunoregulator in the vaccine, could be safely used in horses and ponies.

Cattle were inoculated intramuscularly with up to 1000 μg of endotoxoid and observed at 2 day intervals for 16 days for pyrogenicity, leukopenia and/or leukocytosis, mononuclear cell abnormalicies (differential counts), erythrocyte abnormalicies, lethargy, and diarrhea. N untoward effects were observed in the cattle. It was concluded that up to 1000 μg of endotoxoid could be safely incorporated as an immunoregulator in the vaccine for cattle.

Safety of the Vaccine

The safety of using the vaccine was evaluated relative to the following criteria: 1) Large (up to 5×) doses in laboratory mice, horses and cattle relative to recommended dosage for routine vaccination regimens; 2) Inoculation of horses and cattle with multiple doses within a short time span; 3) The route of inoculation, (i.e., intramuscular, subcutaneous or intraperitoneal); 4) In laboratory mice as a means of future quality control; 5) In laboratory horses and ponies, where multiple criteria could be evaluated; and 6) In field studies, where horses and ponies and cattle in large numbers and of ubiquitous gene pool could be evaluated for a limited number of parameters.

Groups of adult, mixed sex mice (20–25 gm) were inoculated with 1 ml aliquots of the vaccine or components of the vaccine. The mice were observed for mortality, hair coat texture, spinal arching and clustering indicative of peripheral vascular hypothermia, dehydration, lethargy, diarrhea, and abscessation for up to 96 hours.

TABLE 2

Inoculation of Mice with Vaccine

| Group | 96 Hour Survival (%) |
|---|---|
| vaccine/subcutaneous | 100 |
| vaccine/intramuscular | *100 |
| vaccine/intraperitoneal | **70 |
| bacterin/subcutaneous | 100 |
| endotoxoid/subcutaneous | 100 |
| carrier/subcutaneous | 100 |
| carrier/intraperitoneal | ***50 |
| physiological saline | 100 |

*Mice were inoculated intramuscularly with 10–0.1 ml aliquots due to small size.
**Mice died of severe dehydration due to adsorption of serum proteins by the highly lipo-proteinophilic carrier.
***Subsequent intraperitoneal inoculation of 1 ml aliquots, (equivalent to quantity of carrier in 2 ml of vaccine).

The data in Table 2 indicated that 1 ml doses of the vaccine administered either subcutaneously or intramuscularly offered no risk to laboratory mice. However, the peritoneal route of inoculation resulted in 30% mortality due to the high ratio of lipo-proteinophilic carrier to body mass (1:20) and consequent protein dehydration. It was concluded that the adverse effect observed for intraperitoneal inoculation of laboratory mice would be irrelevant since the target species for the vaccine would involve phenomenally greater body weight to carrier ratios, and the recommended route of inoculation would be intramuscular or subcutaneous rather than intraperitoneal.

Healthy, adult horses were inoculated intramuscularly with 2 consecutive 5× ($5 \times 10^{10}$ bacteria, 500 μg endotoxoid) doses of the vaccine, six days apart. The animals were observed daily for 20 days for anorexia, lethargy, diarrhea, dehydration, and tenderness, swelling and/or abscessation at the injection site. The only adverse effect was transient tenderness and swelling at the injection site which subsided within 48–72 hours.

Cattle weighing 500–650 lbs. were vaccinated intramuscularly with 2 consecutive 4.5× (equivalent to $4.5 \times 10^{10}$ bacteria and 437 μg endotoxoid) doses of vaccine 18 days apart. One cow was vaccinated with one 11.25× (equivalent to 1.125×10$^{10}$ bacteria and 1 mg endotoxoid) dose of the vaccine. All animals were examined twice daily for anorexia, lethargy, diarrhea, dehydration, and tenderness, swelling and/or abscessation at the injection site. No adverse reactions were observed in any of the cattle.

The above data indicated that the dose range and regiment recommended for use in horses and cattle offered no untoward risk to the animals.

Healthy, adult horses were inoculated intramuscularly with 2.5× (equivalent to 2.5×10$^{10}$ bacteria and 200 μg endotoxoid) doses of the vaccine at 3 day intervals for 9 days, allowed to rest for 7 days and then the 3 dose—3 day interval inoculation regimen was repeated for 5 additional times. The horses received a total of 18 inoculations over a period of 64 days. Consecutive inoculations were alternated from the neck to buttock. The animals were observed daily for anorexia, lethargy, diarrhea, dehydration; and tenderness, swelling and/or abscessation at injection sites. The only adverse reaction was localized tenderness, circumscribed swelling and abscess formation at two injection sites in one animal after ten inoculations. The abscesses, upon drainage, rapidly resolved and the inoculation regimen was continued. The animals experienced no other adverse reactions.

Calves weighing between 190–650 lbs. were inoculated subcutaneously with 4× (equivalent to 4×10$^{10}$ bacteria and 400 ug endotoxoid) doses of vaccine. Seventeen days later a portion of the calves were re-inoculated intramuscularly with a 1× dose of the vaccine. All animals were observed daily for 120 days for anorexia, lethargy, diarrhea and dehydration. All animals were examined at 3 day intervals for 15 days, followed by 30 day intervals for 120 days thereafter, for weight loss, body temperature, and blood dyscrasias. Five of the calves had firm, circumscribed nodules in the subcutaneous tissue which resorbed by 8–12 days after the primary (4×) subcutaneous inoculation. Similar nodules were inapparent after re-inoculation of the same calves with 1× doses by the intramuscular route.

A herd of horses and ponies were inoculated intramuscularly with 2 doses of vaccine (equivalent to 1×10$^{10}$ bacteria and 100 ug endotoxoid per kg body weight) 14 days apart. Animals were observed daily for 20 days for anorexia, lethargy, diarrhea, dehydration and tenderness, swelling and/or abscessation at injection site. No untoward effects, other than a mild degree of transient tenderness at the injection site in a few animals, were observed.

A herd of feeder cattle weighing between 550–650 lbs. was inoculated with 1 dose of vaccine (equivalent to 1×10$^{10}$ bacteria and 100 μg endotoxoid per kg body weight). A portion of the cattle were inoculated intramuscularly and the balance were inoculated subcutaneously. The cattle were observed daily for 50 days for anorexia, lethargy, diarrhea, and dehydration, tenderness, swelling and/or abscessation at injection sites. No adverse reactions were observed related to the injection sites. No apparent systemic abnormalicies were observed related to the vaccination. No subcutaneous nodulation was apparent in any of the subcutaneously inoculated animals.

In summary, it is apparent that intramuscular or subcutaneous inoculation of cattle, and horses or ponies with the vaccine at reasonable and recommended dose-regimens offers little or no risk to animals.

Efficacy of Vaccine

Healthy, adult horses and ponies were immunized by intramuscular inoculation of two 1× (equivalent to 1×10$^{10}$ bacteria and 100 μg endotoxoid) doses of vaccine approximately two weeks apart. The animals were bled at approximately weekly intervals and antibody titers ascertained by radiolnmunoassay. Immune response curves usually reached a maximum approximately 20–30 days after the primary immunization or 10–20 days after the secondary or anamnestic immunization. Protective efficacy was determined by either carbohydrate engorgement (Per Os) or administration of sublethal doses of endotoxin (intravenously) to vaccinated animals at various times after the secondary immunization. Seventy to eigthy percent of non-vaccinated horses or ponies developed Obel grade 3–4, acute laminitis by forty to fifty hours after carbohydrate engorgement with a cornstarch-wood flour gruel administered via stomach tube at the dosage of 17.6 gram gruel per kilogram body weight. One hundred percent (100%) of non-vaccinated horses or ponies developed tachypnea, dyspnea and ataxia within 2–3 minutes and passed fluid, non-formed stools by 45 minutes after intravenous administration of endotoxin at dosage of 10 ug per kilogram body weight.

TABLE 3

Challenge of Vaccinated Horses by Carbohydrate Overload and IV-Endotoxin

| Challenge | Combination Vaccine | Placebo |
| --- | --- | --- |
| CHO- (Per Os) | *2/19 (10.5%) | 75–85% |
| Endotoxin (IV) | *3/8 (37.5%) | 100% |
| Total | *5/27 (18.5%) | |

*Number of animals that developed Obel grade (3–4) laminitis or endotoxin-mediated symptomology after challenge.

Table 3 indicates that approximately 90% of the vaccinated animals, compared with 15 to 25% of the non-vaccinated-control pool (consisting of 100 animals over 12–14 years) failed to develop Obel grade 3–4 laminitis after challenge by carbohydrate overload, suggesting at least a 65–75% protective efficacy. Similar comparison of the vaccinated and non-vaccinated horses challenged with sublethal endotoxin, indicates a greater than 60% protective efficacy. Consequently, it was concluded that vaccination of normal, adult horses or ponies with two 1× doses of vaccine resulted in protection of up to 90% of the animals from carbohydrate-induced laminitis (i.e., founder) and greater than 60% from endotoxin-induced endotoxemia.

A group of cattle of mixed age and sex were vaccinated subcutaneously with one or two doses of vaccine. Animals were bled and sera obtained at 3 day intervals for 15 days, and then at 30 day intervals for up to 120 days. Antibody titers were determined by radioimmunoassay. All animals had developed 2 to 4 fold increases in antibody titer by 20 days after vaccination. Detectable titers were present in approximately 70% of the animals at 120 days after vaccination. A portion of the group was placed on a high carbohydrate ration thirty days after vaccination and after 17 weeks had not developed any signs of anorexia, diarrhea, lameness or sudden death syndrome.

A herd of feeder cattle weighing between 550–680 lbs. were vaccinated with 1-(1×) dose of vaccine and monitored daily for diarrheal disease, lameness and sudden death. No diarrheal disease, lameness or mortality occurred during 11 weeks of observation.

The Serum

The development and therapeutic use of hyperimmune serum was based on the rationale that non-vaccinated animals with clinically apparent endotoxin-associated diseases are not afforded the time necessary for their own immune systems to build protective levels of antibodies, after vaccination with the combination vaccine. Thus, passive immunization with pre-existing, stored antibodies developed by another animal (hyperimmune serum) provided a means of short-term protection that could aid in amelioration of the endotoxin-associated disease until the animal's own immune system was sufficiently protective. An acute laminitic episode in the non-vaccinated horse that accidentally gets into the grain bin and subsequently founders, is a classic example with current implication in the horse industry.

The hyperimmune serum is comprised of clot serum or plasma, or parts thereof (gamma globulin, immunoglobulin, or immunoglobulin IgGT) which contain antibody(s) specific for the core component (2-Keto-3-deoxyoctonic Acid-Lipid A) in endotoxin of bacteria in the taxonomic family Enterobacteriaceae which are elicited by hyperimmunization of animals with the combination vaccine.

Hyperimmune sera is prepared by intramuscular injection of healthy adult horses with 6 consecutive 2.5 ml doses of the combination vaccine at 3 day intervals followed by 2 consecutive 2.5 ml doses at 7 day intervals. Serum samples are taken from the horses prior to vaccination and at 3 day intervals thereafter for serologic analyses. Concentrations of antigen-specific immunoglobulins (IgG, GT, A and M) are determined by radio-immunoassay using $^{125}$I-protein A. When each animal's immune response has reached a high-titer plateau, 12 liter quantities whole blood are collected via vena puncture. The hyperimmune sera is obtained by centrifugation after coagulation (approximately 24 hr.), and then heat inactivated (56° C., 30 min.) and stored at 4° C. until use or subsequent purification of gamma globulin or immunoglobulin.

Gamma globulin is prepared by precipitation from aliquots of hyperimmune sera with 50% saturated ammonium sulfate (SAS). The precipitate is then resuspended in 0.01 M phosphate buffer (PB, $NaH_2PO_4$—$Na_2HPO_4$, pH 8) and exhaustively dialyzed against the same buffer to remove the SAS.

The gamma globulin obtained from 50 ml aliquots of hyperimmune sera is absorbed onto a column (5×50 cm) of diethylaminoethyl (DEAE) cellulose equilibrated with PB, pH 8. The column is developed initially with equilibrating buffer (PB, pH 8) to elute IgG, followed by the addition of a NaCl gradient (00.3 M) to the PB to disassociate IgG(T). The eluate is collected in 5 ml aliquots using a refrigerated fraction collector and elution peaks monitored continuously using a Beckman DB-GT Spectrophotometer and dual wavelength of 360 and 380 nm. Protein concentration is determined using the Warberg-Christian constant and confirmed by the Lowry method. The IgG(T) aliquots are pooled, lyophilized and stored at −40 C. for subsequent use in passive immunization. Horses, experimentally foundered by overfeeding with carbohydrate or intravenous injection of bacterial endotoxins showed rapid improvement upon administration of hyperimmune serum, obtained from other horses vaccinated with the combination vaccine. Similarly, death from intravenous injection of bacterial endotoxins is precluded in laboratory mice by immunization with hyperimmune serum obtained from horses vaccinated with the combination vaccine.

Safety, Potency and Efficacy of Hyperimmune Serum

Groups of healthy, male adult (20 gm), (CF-1) mice were inoculated, intraperitoneally (IP) with 1 ml aliquots of 100%, 10% or 0.1% of whole, equine hyperimmune serum on four (4) consecutive days. The animals were observed for four days at 12 hour intervals for dyspnea, rigor, nose and tail perfusion, swollen eyes, coat texture and death. No untoward effects were observed from the IP serum injections.

A healthy adult pony was inoculated with 700 ml of hyperimnmune serum admixed with 1000 ml of Lactated Ringers Solution, by intravenous (IV) drip over 90 minutes. The animal was monitored for 6½ hours (at 10–15 minute intervals) for change in body temperature, heart rate, peripheral perfusion, and discomfort and/or distress. The pony experienced no signs of discomfort or stress. The body temperature and heart rate exhibited slight (statistically insignificant) increases (100.4°→101.3° F.; 40→56 beats/min.) Approximately 60–90 minutes after initiation of the IV-drip.

In a clinic trial, a 900 lb. horse with complications associated from septic shock was inoculated intravenously with 1200 ml hyperimmune serum continuously over a period of 10 hours in Lactated Ringers solution. The animal exhibited no untoward signs of toxicity and indeed showed marked improvement.

To evaluate the safety of intramuscular inoculation, healthy, adult ponies were inoculated intramuscularly (IM) with 0, 10, 20, and 40 ml of hyperimmune serum. The animals were monitored at 30 min., 1, 2, 4, 8, 16, and 24 hours after inoculation for (1) urination; (2) diarrhea; (3) rigors; (4) peripheral perfusion; (5) temperature; (6) respiration; (7) heart rate; (8) leukocytosis (or -penia); and (9) erythrocytosis (or -penia). No untoward effects were observed. A diffuse nodule was apparent in the neck of one pony administered the 40 ml dose intramuscularly which had receded by 4 hours.

Figure 2:
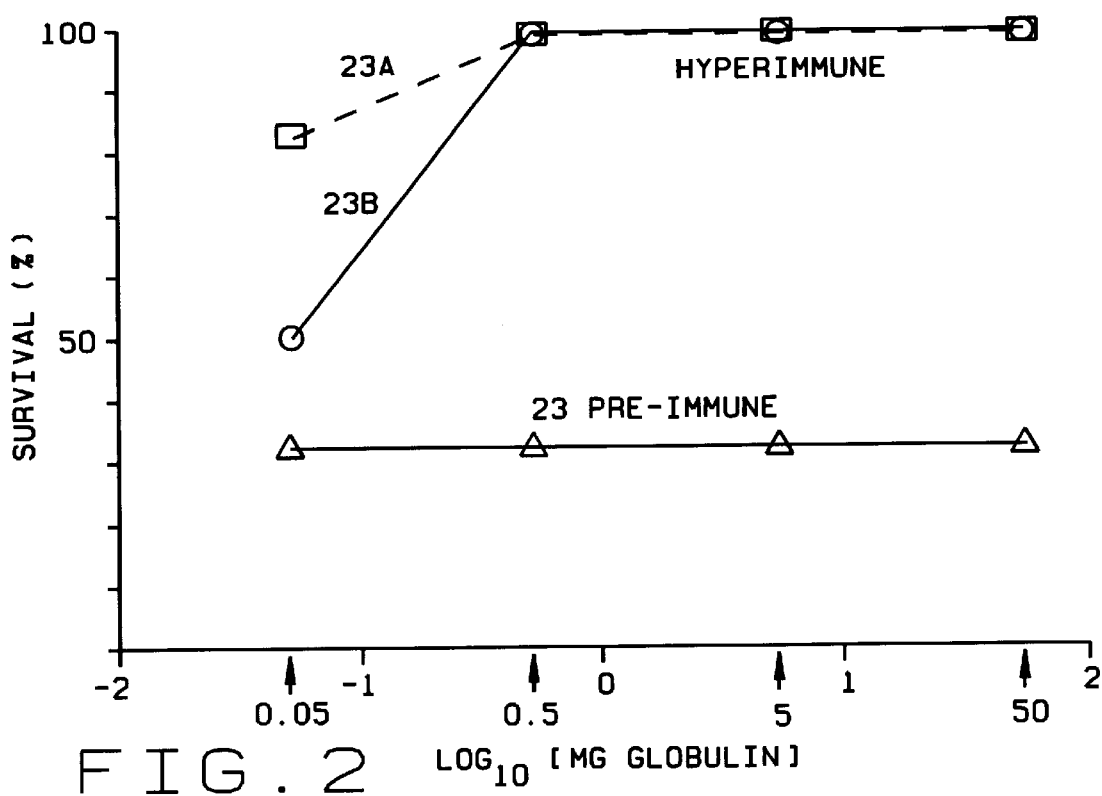
FIG. 2 is a graph containing pre-immune and hyperimmune globulin of horse #23 using a passive immunization mouse model.
Figure 3:
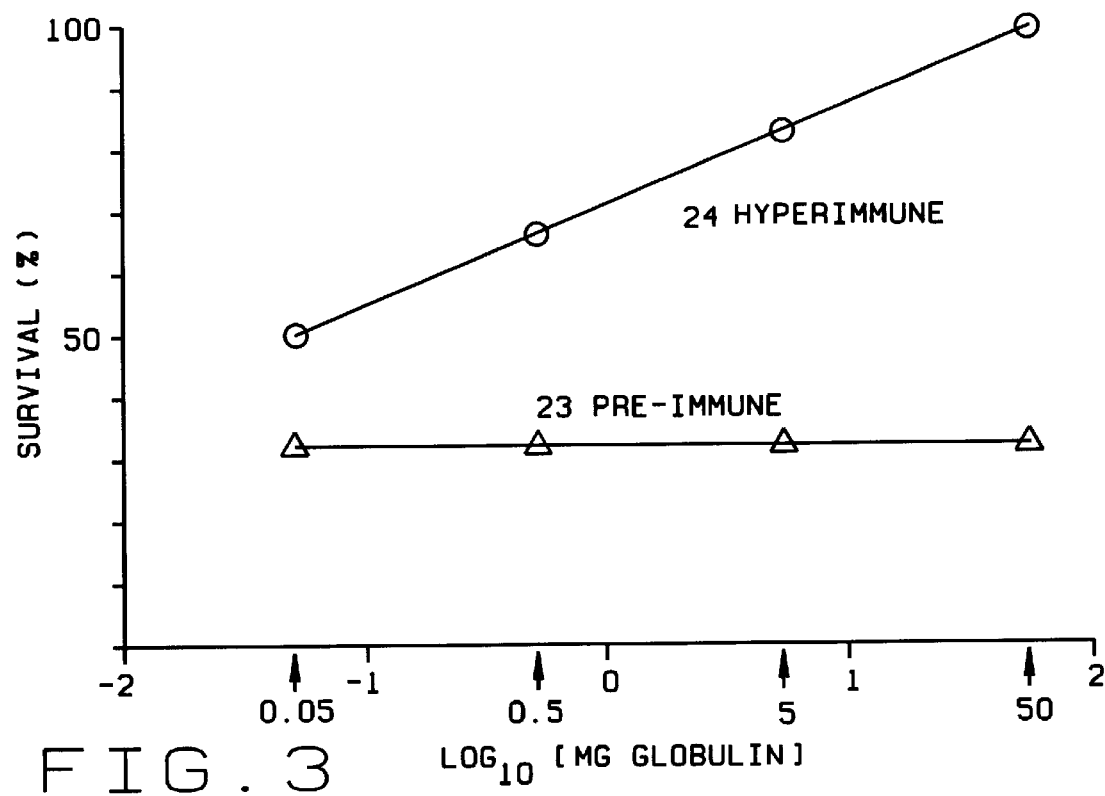
FIG. 3 is a graph comparing pre-immune and hyperimmune globulin of horse #24 using a passive immunization mouse model.

Gamma globulin, containing the protective antibody, was extracted from the hyperimmune sera in order to evaluate protective efficacy on a milligrams-protein basis. Pre-immune and hyperimmune sera from individual horses hyperimmunized with vaccine were compared by inoculating subsets of CF-1 mice with various concentrations of gamma globulin in divided doses on two consecutive days before intravenous challenge with endotoxin. The data in FIGS. 2 and 3 compare pre-immune and hyperimmune globulin from two separate horses (#23 and #24) using the passive immunization mouse model. Hyperimmune globulin was prepared from horse #23 at two subsequent times after hyperimmunization (#23A, #23B). Comparison of the percentages of mice surviving 96 hours after endotoxin challenge that were passively immunized with 50 ug or more of #23 pre-immune or hyperimmune (#23A and #23B) globulin indicates at least a 20 (for #23B) to 50 (for #23A) percent increase in survival for those subsets receiving hyperimmune globulin (FIG. 2). Comparison of #24 pre-immune with #24 hyperimmune also indicates similar protective efficacy but to a lesser degree (FIG. 3). It was concluded that the hyperimmune serum contains antibodies which can passively protect mice from lethal endotoxin challenge.

The efficacy of the hyperimmune gamma globulin was ascertained by challenge (endotoxin or carbohydrate engorgement) of subsets of horses and ponies after intravenous inoculation with 5, 15, or 20 mg antibody protein/kg body weight. All animals received a mixture of #23A and #23B hyperimmune gamma globulin. Combination of the two preparations was necessary in order to insure adequate quantities of the known antibody protein to complete the studies. Protection was defined as the marked delay and/or amelioration of the immediate vital sign changes, and development of equal to or less than Obel Grade 2 disease, in sublethal endotoxin and/or carbohydrate challenged animals.

TABLE 4

Passive Immunization of Horses with Pre-Immune and Hyperimmune Serum

| Challenge | Passive Immunization with | |
| --- | --- | --- |
| | Hyperimmune globulin | Pre-Immune globulin |
| CHO- (Per Os) | 40% | 100% |
| Endotoxin (IV) | 0% | 50% |

Percentage figures represent developing Obel grade (3–4) laminitis or endotoxin mediated symptomology after challenge.

Conclusion

The advantage of the combination vaccine is that it is prophylactic in nature, in opposition to current treatment modes which are initiated retrospectively or only after development of disease. An added advantage of the combination vaccine is that immunized animals develop an earlier and higher degree of protection from many of the endotoxin associated diseases without the risks inherent in existing vaccines such as (a) provoking potentially fatal anaphylaxis; (b) developing potentially fatal infections by reversion of live, non-pathogenic bacterins to pathogenic forms; or (c) losing ability to elicit protection because of relative changes in strains of bacteria causing disease. The detoxified endotoxin component of the combination vaccine, as a potent immune modulator with propensity for B-lymphocytes causes not only more rapid proliferation of these antibody progenitor cells, but also their earlier occurrence in the activated functional state, thus resulting in production of protective levels of antibody in the host's circulation much sooner after vaccination than observed for conventional bacterin vaccines. The bacterin component of the combination vaccine, comprised of a mutant exhibiting a naked core antigen (2-Keto-3-deoxyoctonic Acid-Lipid A), devoid of any of the O-carbohydrate side chains (K Antigens) present in conventional bacterin vaccines, precludes the development of O-carbohydrate specific Immunoglobulin E (IgE, Reagin) and thus elicitation of IgE-medi ted anaphylaxis after vaccination. Since the naked core antigen, in contrast to O-carbohydrate side chains (K-antigens serotypes), is common to many Gram negative bacteria, it elicits antibodies of broad cross-protection, while also precluding the 1055 of protective efficacy because of epidemiological shifts and drifts in O-carbohydrate side chains (K-antigens, serotypes) relative to time.

Prior to the development of the combination vaccine and hyperimmune serum elicited by the combination vaccine, medical management involved primarily chemotherapy only after onset of the Endotoxin-associated diseases. The advantage of hyperimmune serum, is that in the non-vaccinated animal with clinically apparent disease, it may ameliorate the disease process, thus precluding crippling and/or death in the horse or other species.

From the foregoing, it will be seen that this invention is one well adapted to attain all the ends and objects hereinabove set forth together with other advantages which are obvious and which are inherent to the structure.

It will be understood that certain features and subcombinations are utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, we claim:

1. A hyperimmune serum for treating Gram negative bacterial diseases, said serum produced by the process comprising:

combining a killed suspension of non-O-carbohydrate side chain bacterial mutant ATCC 53000 as a bacterin, a detoxified lipopolysaccharide as the immune modulator having specific propensity for B-lymphocytes to cause rapid proliferation of antibody progenitor cells and their earlier occurrence, thus resulting in enhanced production of protective and neutralizing antibodies in a host's circulation against intact endotoxin and bacteria, and a protein and lipid binding carrier having high lipophilic and high proteinophilic affinity to ensure uniform component suspension and prolonged antigenic release as a vaccine;

vaccinating a donor animal with said vaccine to produce antigen specific antibodies in response to said vaccine;

collecting whole blood from said donor animal; and forming clot serum containing said antigen specific antibodies from said whole blood.

2. The serum as in claim 1, including vaccinating a donor animal with said vaccine to produce antigen specific antibodies for protection against diseases caused by Gram negative bacteria in the taxonomic family Enterobacteriaceae.

3. The serum as in claim 1, including vaccinating a donor animal with said vaccine to produce antigen specific antibodies for protection against diseases caused by bacteria selected from the group consisting of *Salmonella enteritidis, Salmonella typhimurium, Salmonella typhosa, Salmonella minnesota, Salmonella abortus-equi*, and *Escherichia coli*.

4. A method for treating an animal diseased with a Gram negative bacterial disease, the steps of said method comprising:

combining a killed suspension of non-O-carbohydrate side chain bacterial mutant ATCC 53000 as a bacterin, a detoxified lipopolysaccharide as the immune modulator having specific propensity for B-lymphocytes to cause rapid proliferation of antibody progenitor cells and their earlier occurrence, thus resulting in enhanced production of protective and neutralizing antibodies in a host's circulation against intact endotoxin and bacteria, and a protein and lipid binding carrier having high lipophilic and high proteinophilic affinity to ensure uniform component suspension and prolonged antigenic release as a vaccine;

vaccinating a donor animal with said vaccine to produce antigen specific antibodies in response to said vaccine;

collecting whole blood from said donor animal;

forming clot serum containing said antigen specific antibodies from said whole blood; and introducing into said diseased animal sufficient serum to establish a protective level of said antigen specific antibodies.

5. The method as in claim 4, including vaccinating a donor animal with said vaccine to produce antigen specific antibodies for protection against diseases caused by Gram negative bacteria in the taxonomic family Enterobacteriaceae.

6. The method as in claim 4, including vaccinating a donor animal with said vaccine to produce antigen specific antibodies for protection against diseases caused by bacteria selected from the group consisting of *Salmonella enteritidis, Salmonella typhimurium, Salmonella typhosa, Salmonella minnesota, Salmonella abortus-equi*, and *Escherichia coil*.

* * * * *